US006723748B2

(12) United States Patent
Klimko et al.

(10) Patent No.: US 6,723,748 B2
(45) Date of Patent: *Apr. 20, 2004

(54) USE OF CLOPROSTENOL AND FLUPROSTENOL ANALOGUES TO TREAT GLAUCOMA AND OCULAR HYPERTENSION

(75) Inventors: Peter G. Klimko, Fort Worth, TX (US); John E. Bishop, Groton, MA (US); Verney L. Sallee, Burleson, TX (US); Paul W. Zinke, Fort Worth, TX (US)

(73) Assignee: Alcon Manufacturing, Ltd., Fort-Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/068,027

(22) Filed: Feb. 5, 2002

(65) Prior Publication Data

US 2002/0111381 A1 Aug. 15, 2002

Related U.S. Application Data

(63) Continuation of application No. 09/777,409, filed on Feb. 6, 2001, now Pat. No. 6,344,478, which is a continuation of application No. 09/281,043, filed on Mar. 30, 1999, now Pat. No. 6,184,250, which is a continuation-in-part of application No. 08/917,795, filed on Aug. 21, 1997, now Pat. No. 5,889,052, which is a continuation of application No. 08/769,293, filed on Dec. 18, 1996, now Pat. No. 5,665,773, which is a continuation of application No. 08/280,681, filed on Jul. 26, 1994, now abandoned, which is a continuation-in-part of application No. 08/101,598, filed on Aug. 3, 1993, now Pat. No. 5,510,383.

(51) Int. Cl.[7] ............................................. A61K 31/215
(52) U.S. Cl. ...................... 514/530; 514/573; 514/913
(58) Field of Search ................................. 514/530, 573, 514/913

(56) References Cited

U.S. PATENT DOCUMENTS

| | | |
|---|---|---|
| 3,954,881 A | 5/1976 | Bowler |
| 4,159,343 A | 6/1979 | Skuballa et al. |
| 4,256,745 A | 3/1981 | Skuballa et al. |
| 4,321,275 A | 3/1982 | Bowler et al. |
| 4,599,353 A | 7/1986 | Bito |
| 4,952,581 A | 8/1990 | Bito et al. |
| 5,151,444 A | 9/1992 | Ueno et al. |
| 5,173,507 A | 12/1992 | DeSantis et al. |
| 5,288,754 A | 2/1994 | Woodward et al. |
| 5,352,708 A | 10/1994 | Woodward et al. |
| 5,422,368 A | 6/1995 | Stjernschantz et al. |
| 5,480,900 A | 1/1996 | DeSantis et al. |
| 5,510,383 A | 4/1996 | Bishop et al. |
| 5,565,492 A | 10/1996 | DeSantis et al. |
| 5,605,922 A | 2/1997 | DeSantis et al. |
| 5,665,773 A | 9/1997 | Klimko et al. |
| 5,773,471 A | 6/1998 | Oguchi et al. |
| 5,811,443 A | 9/1998 | DeSantis et al. |

FOREIGN PATENT DOCUMENTS

| | | |
|---|---|---|
| EP | 308 135 A2 | 3/1989 |
| EP | 330 511 A2 | 8/1989 |
| EP | 364 417 A1 | 4/1990 |
| EP | 366 279 A2 | 5/1990 |
| EP | 435 682 A2 | 7/1991 |
| EP | 603 800 A1 | 6/1994 |
| GB | 1350971 | 4/1974 |
| GB | 1486832 | 9/1977 |
| WO | 90/02553 | 3/1990 |
| WO | 94/06433 | 3/1994 |

OTHER PUBLICATIONS

Bito et al., "The Ocular Effects of Prostaglandins and the Therapeutic Potential of New $PGF_{2\alpha}$ Analog, PhXA41 (latanoprost), for Glaucoma Management," *J. of Lipid Mediators*, 6:535–543 (1993).

Burke et al., "Prostaglandin $F_{2\alpha}$ Effects on Rabbit IOP Negatively Correlate With Classical $PGF_{2\alpha}$ Receptor Stimulation" ARVO, Sarasota, Florida, vol. 29, p. 325, May 1–6, 1988.

Coleman, et al., "Prostanoids and their Receptors," *Comprehensive Medicinal Chemistry*, vol. 3, 12.11:643–714.

Narumiya et al., "Structure and Function of Prostanoid Receptors," *J. of Lipid Mediators*, 6:155–161 (1993).

Resul et al., "Phenyl–Substituted Prostaglandins: Potent and Selective Antiglaucoma Agents," *J. Med. Chem.*, 36:243–248 (1993).

Stjernschantz et al., "Phenyl Substituted Prostaglandin Analogs for Glaucoma Treatment," *Drugs of the Future*, 17(8):691–704 (1992).

Woodward et al., "Intraocular Pressure Effects of Selective Prostanoid Receptor Agonists Involve Different Receptor Subtypes According to Radioligand Binding Studies," *J. of Lipid Mediators*, 6:545–553 (1993).

Zajacz et al., "Effect on Human Eye of Prostaglandin and a Prostaglandin Analogue Used to Induce Abortion," *IRCS Medical Science: Clinical Medicine: Clinical Pharmacology & Therapeutics: Drug Metabolism & Toxicology: The Eye: Reproduction, Obstetrics & Gynecology*, 4:316 (1976).

*The Merck Index*, 11th Ed., p. 375 (1989).
*The Merck Index*, 11th Ed., pp. 656–657 (1989).

Woodward et al., "Definition of Prostanoid Receptor Subtypes by Radioligand Binding and the Effects of Selective Agonists on Intraocular Pressure" *Ex. Eye Res.* 55(1):s91 (1992).

Primary Examiner—Zorreh Fay
(74) Attorney, Agent, or Firm—Barry L. Copeland

(57) ABSTRACT

Disclosed is the use of cloprostenol and fluprostenol analogues in combination with carbonic anhydrase inhibitors for the treatment of glaucoma and ocular hypertension and ophthalmic compositions therefor.

15 Claims, No Drawings

USE OF CLOPROSTENOL AND FLUPROSTENOL ANALOGUES TO TREAT GLAUCOMA AND OCULAR HYPERTENSION

CROSS REFERENCE TO RELATED APPLICATIONS

The present application is a continuation of U.S. patent application Ser. No. 09/777,409, filed Feb. 6, 2001, now U.S. Pat. No. 6,344,478, which is a continuation of U.S. patent application Ser. No. 09/281,043, filed Mar. 30, 1999, now U.S. Pat. No. 6,184,250, which is a continuation-in-part of U.S. patent application Ser. No. 08/917,795, filed Aug. 21, 1997, now U.S. Pat. No. 5,889,052, which is a continuation of U.S. patent application Ser. No. 08/769,293, filed Dec. 18, 1996, now U.S. Pat. No. 5,665,773, which is a continuation of U.S. patent application Ser. No. 08/280,681, filed Jul. 26, 1994, now abandoned, which is a continuation-in-part of U.S. patent application Ser. No. 08/101,598 filed Aug. 3, 1993, now U.S. Pat. No. 5,510,383.

BACKGROUND OF THE INVENTION

The present invention relates to the treatment of glaucoma and ocular hypertension. In particular, the present invention relates to the use of cloprostenol and fluprostenol analogues for the treatment of glaucoma and ocular hypertension.

Cloprostenol and fluprostenol, both known compounds, are synthetic analogues of $PGF_{2\alpha}$ a naturally-occurring F-series prostaglandin (PG). Structures for $PGF_{2\alpha}$ (I), cloprostenol (II), and fluprostenol (III), are shown below:

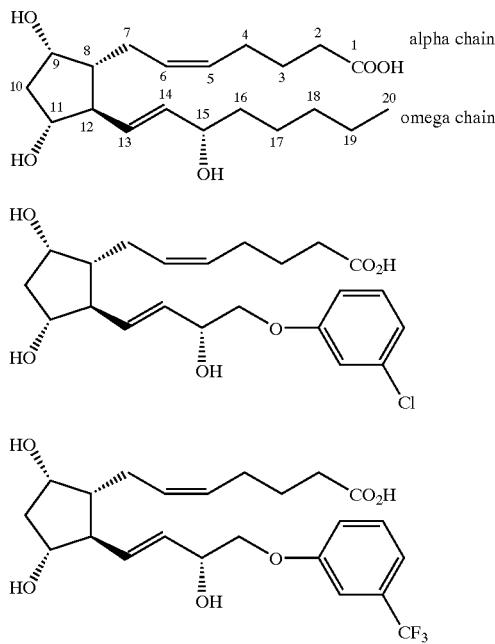

The chemical name for cloprostenol is 16-(3-chlorophenoxy)-17,18,19,20-tetranor $PGF_{2\alpha}$. Monograph No. 2397 (page 375) of *The Merck Index*, 11th Edition (1989) is incorporated herein by reference to the extent that it describes the preparation and known pharmacological profiles of cloprostenol. Fluprostenol has 15 the chemical name 16-(3-trifluoromethylphenoxy)-17,18,19,20-tetranor $PGF_{2\alpha}$. Monograph No. 4121 (pages 656–657) of *The Merck Index*, 11th Edition (1989) is incorporated herein by reference to the extent that it describes the preparation and known pharmacological profiles of fluprostenol. Cloprostenol and fluprostenol are 16-aryloxy PGs and, in addition to the substituted aromatic ring, differ from the natural product $PGF_{2\alpha}$ in that an oxygen atom is embedded within the lower (omega) chain. This oxygen interruption forms an ether functionality.

Naturally-occurring prostaglandins are known to lower intraocular pressure (IOP) after topical ocular instillation, but generally cause inflammation, as well as surface irritation characterized by conjunctival hyperemia and edema. Many synthetic prostaglandins have been observed to lower intraocular pressure, but such compounds also produce the aforementioned side effects which severely restrict clinical utility.

SUMMARY OF THE INVENTION

It has now been unexpectedly found that certain novel cloprostenol and fluprostenol analogues are useful in treating glaucoma and ocular hypertension. In particular, topical application of ophthalmic compositions comprising these novel cloprostenol and fluprostenol analogues result in significant IOP reduction.

DETAILED DESCRIPTION OF THE INVENTION

The compounds useful in the present invention have the following general formula:

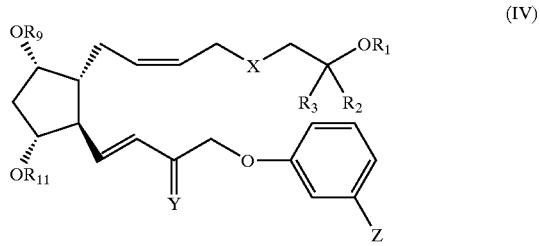

(IV)

wherein:
$R_1$=H; $C_1$–$C_{12}$ straight-chain or branched alkyl; $C_1$–$C_{12}$ straight-chain or branched acyl; $C_3$–$C_8$ cycloalkyl; or a cationic salt moiety;

$R_2$, $R_3$=H, or $C_1$–$C_5$ straight-chain or branched alkyl; or $R_2$ and $R_3$ taken together may represent O;

X=O, S, or $CH_2$;

⚏ represents any combination of a single bond, or a cis or trans double bond for the alpha (upper) chain; and a single bond or trans double bond for the omega (lower) chain;

$R_9$=H, $C_1$–$C_{10}$ straight-chain or branched alkyl, or $C_1$–$C_{10}$ straight-chain or branched acyl;

$R_{11}$=H, $C_1$–$C_{10}$ straight-chain or branched alkyl, or $C_1$–$C_{10}$ straight-chain or branched acyl;

Y=O; or H and $OR_{15}$ in either configuration wherein $R_{15}$=H, $C_1$–$C_{10}$ straight-chain or branched alkyl, or $C_1$–$C_{10}$ straight-chain or branched acyl; and Z=Cl or $CF_3$;

with the proviso that when $R_2$ and $R_3$ taken together represent O, then $R_1 \neq C_1$–$C_{12}$ straight-chain or branched acyl; and when $R_2$=$R_3$=H, then $R_1 \neq$ a cationic salt moiety.

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon—carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon—carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "cationic salt moiety" includes alkali and alkaline earth metal salts as well as ammonium salts.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Preferred compounds include: cloprostenol isopropyl ester (Table 1, compound 1A), fluprostenol isopropyl ester (compound 1B), 16-phenoxy-17,18,19,20-tetranor $PGF_{2\alpha}$ isopropyl ester (compound 2), 17-phenyl-18,19,20-trinor $PGF_{2\alpha}$, isopropyl ester (compound 3), 13,14-dihydro-17-phenyl-18,19,20-trinor $PGF_{2\alpha}$) isopropyl ester (compound 4), the 3-oxa form of cloprostenol isopropyl ester (Table 2, compound 5), 13,14-dihydrofluprostenol isopropyl ester (compound 6), cloprostenol-1-ol (compound 7), and 13,14-dihydrocloprostenol-1-ol pivaloate (compound 8).

TABLE 1

| COMPOUND NAME | COMPOUND STRUCTURE |
| --- | --- |
| 1A Cloprostenol, isopropyl ester | 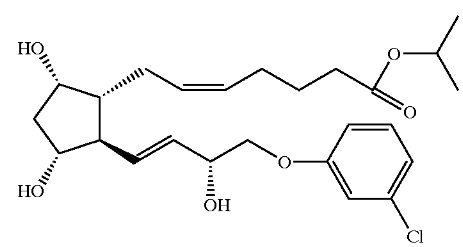 |
| 1B Fluprostenol, isopropyl ester | 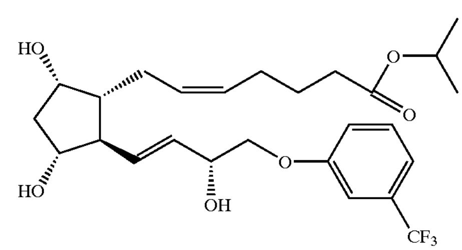 |

TABLE 1-continued

| | COMPOUND NAME | COMPOUND STRUCTURE |
|---|---|---|
| 2 | 16-Phenoxy-17,18,19,20-tetranor $PGF_{2\alpha}$, isopropyl ester | 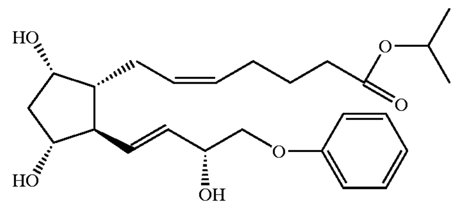 |
| 3 | 17-Phenyl-18,19,20-trinor $PGF_{2\alpha}$, isopropyl ester | 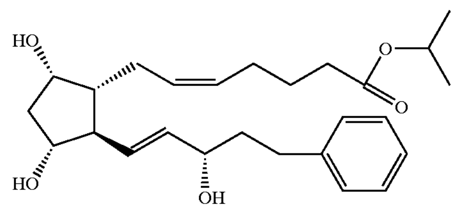 |
| 4 | 13,14-Dihydro-17-phenyl-18,19,20-trinor $PGF_{2\alpha}$, isopropyl ester | 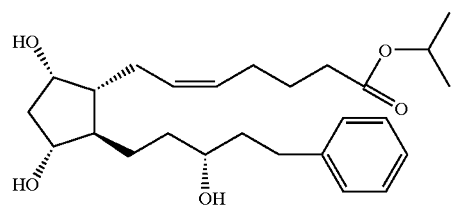 |

TABLE 2

| | COMPOUND NAME | COMPOUND STRUCTURE |
|---|---|---|
| 5 | 3-oxacloprostenol isopropyl ester | 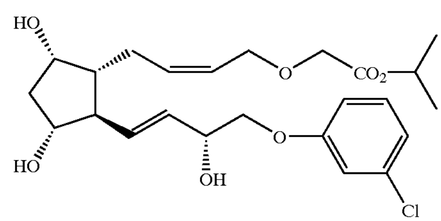 |
| 6 | 13,14-dihydrofluprostenol isopropyl ester | 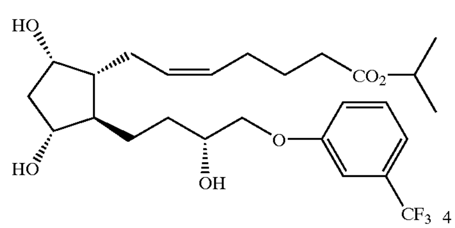 |
| 7 | cloprostenol-1-ol | 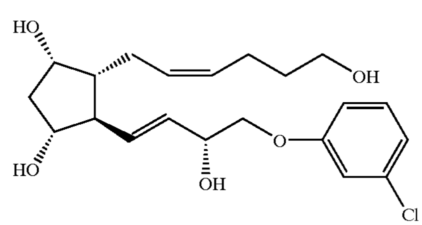 |

TABLE 2-continued

| COMPOUND NAME | COMPOUND STRUCTURE |
|---|---|
| 8  13,14-dihydrocloprostenol-1-ol pivaloate | (structure shown) |

The compounds of formula (IV) are useful in lowering intraocular pressure and thus are useful in the treatment of glaucoma. Such compounds are also useful in improving optic nerve head blood flow and the treatment of optic nerve disorders (including without limitation retarding visual field loss and improving visual acuity), the latter being generally described in U.S. Pat. No. 5,773,471, the contents of which are by this reference incorporated herein. It is further contemplated that the compounds of the present inventions can be used with other medicaments known to be useful in the treatment of glaucoma or ocular hypertension, either separately or in combination. For example, the prostaglandin analogs of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443); and (iv) cholinergic agonists, such as pilocarpine. The disclosures of U.S. Pat. Nos. 4,952,581 and 5,811,443 are incorporated herein by this reference. The preferred route of administration is topical. The dosage range for topical administration is generally between about 0.01 and about 1000 micrograms per eye (μg/eye), preferably between about 0.1 and about 100 μg/eye, and most preferably between about 1 and 10 μg/eye. The compounds of the present invention can be administered as solutions, suspensions, or emulsions (dispersions) in a suitable ophthalmic vehicle.

In forming compositions for topical administration, the compounds of the present invention are generally formulated as between about 0.00003 to about 3 percent by weight (wt %) solutions in water at a pH between 4.5 to 8.0. The compounds are preferably formulated as between about 0.0003 to about 0.3 wt % and, most preferably, between about 0.003 and about 0.03 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.
Antimicrobial Preservatives:

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M®, or other agents known to those skilled in the art. Such preservatives are typically employed at a concentration between about 0.001% and about 1.0% by weight.
Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; Tyloxapol ®; Cremophor® EL; sodium dodecyl sulfate; glycerol; PEG 400; propylene glycol; cyclodextrins; or other agents known to those skilled in the art. Such co-solvents are typically employed at a concentration between about 0.01% and about 2% by weight.
Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a concentration between about 0.01% and about 2% by weight.

The following Examples 1–4 describe the synthesis of compounds 5–8 (Table 2). These syntheses are representative in nature and are not intended to be limiting. Other compounds of formula (IV) may be prepared using analogous techniques known to those skilled in the art.

In the examples below, the following standard abbreviations are used: g=grams (mg=milligrams); mol=moles (mmol=millimoles); mol %=mole percent; mL=milliliters; mm Hg=millimeters of mercury; mp=melting point; bp=boiling point; h=hours; and min=minutes. In addition, "NMR" refers to nuclear magnetic resonance spectroscopy and "CI MS" refers to chemical ionization mass spectrometry.

EXAMPLE 1

Synthesis of 3-Oxacloprostenol (5)

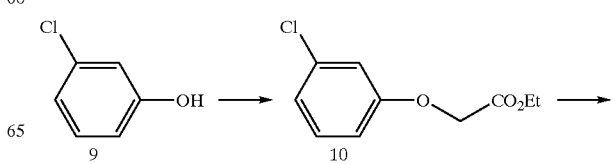

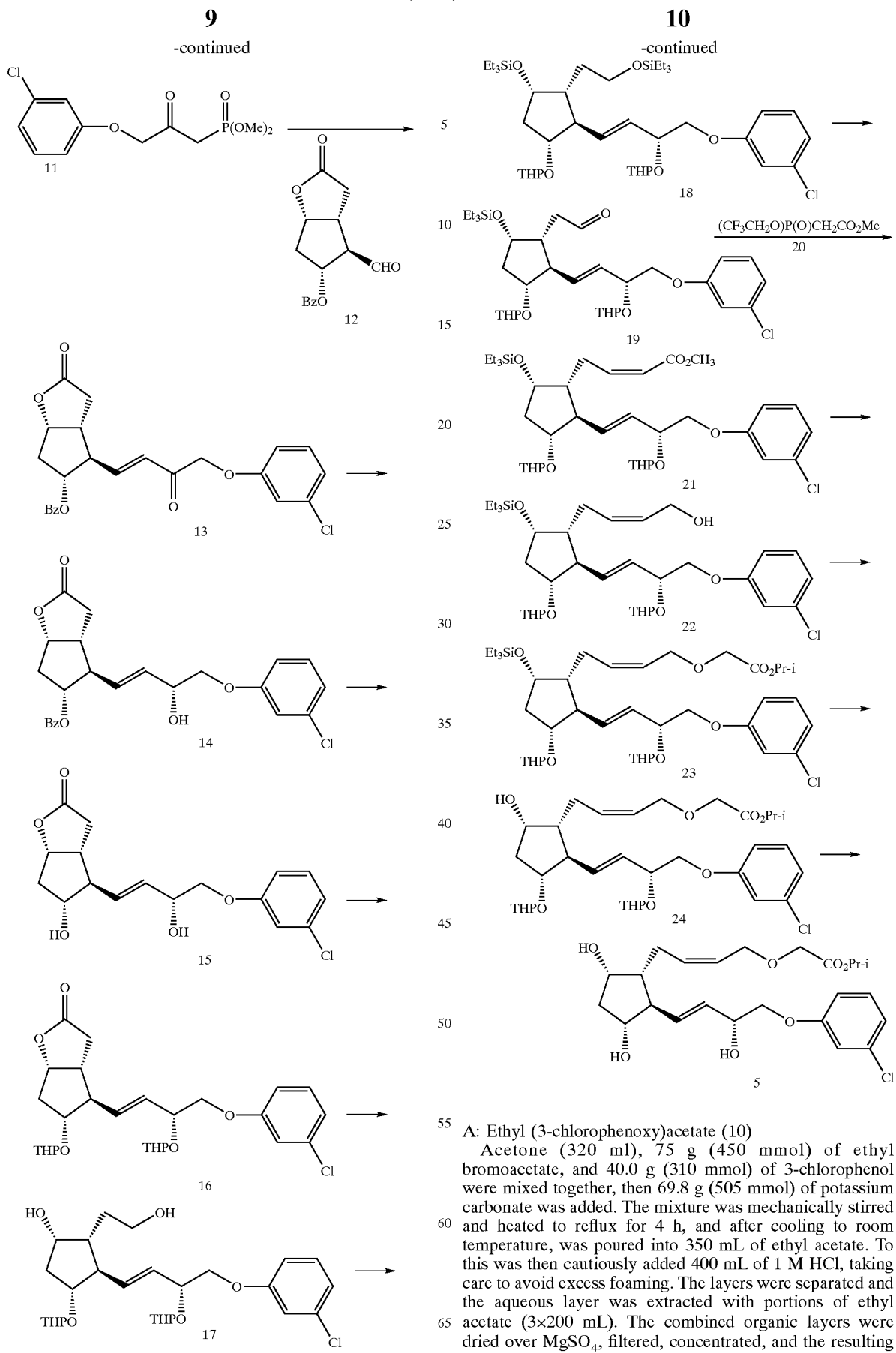

A: Ethyl (3-chlorophenoxy)acetate (10)

Acetone (320 ml), 75 g (450 mmol) of ethyl bromoacetate, and 40.0 g (310 mmol) of 3-chlorophenol were mixed together, then 69.8 g (505 mmol) of potassium carbonate was added. The mixture was mechanically stirred and heated to reflux for 4 h, and after cooling to room temperature, was poured into 350 mL of ethyl acetate. To this was then cautiously added 400 mL of 1 M HCl, taking care to avoid excess foaming. The layers were separated and the aqueous layer was extracted with portions of ethyl acetate (3×200 mL). The combined organic layers were dried over MgSO$_4$, filtered, concentrated, and the resulting solid was recrystallized from hexane to afford 58 g (87%) of 10 as a white solid, m.p.=39–40° C. $^1$H NMR δ 7.20–7.08 (m, 1 H), 6.95–6.82 (m, 2 H), 6.75–6.70 (m, 1 H), 4.53 (s, 2 H), 4.21 (q, J=7.2 Hz, 2 H), 1.23 (t, J=7.2 Hz, 3 H).

B: Dimethyl [3-(3-chlorophenoxy)-2-oxoprop-1-yl] phosphonate (11)

To 20.6 g (166 mmol, 238 mol %) of dimethyl methylphosphonate in 110 mL of THF at −78° C. was added dropwise 65 mL (162 mmol, 232 mol %) of a 2.5 M solution of n-BuLi in hexanes. After addition was complete, the mixture was stirred for an additional 1 h, after which 15.0 g (69.9 mmol) of aryloxyester 10 in 40 mL of THF was added dropwise. The reaction was stirred for 1 h and then quenched by the addition of 100 mL of saturated NH$_4$Cl. The mixture was poured into 200 mL of a 1/1 mixture of saturated NaCl/ethyl acetate, layers were separated, and the aqueous layer was further extracted with ethyl acetate (2×100 mL). Combined organic layers were dried over MgSO$_4$, filtered, and concentrated, to afford 20.5 g (100%) of 11 as a viscous oil. $^1$H NMR δ 7.22 (t, J=8.1 Hz, 1 H), 7.05–6.90 (m, 2 H), 6.85–6.78 (m, 1 H), 4.72 (s, 2 H), 3.84 (s, 3 H), 3.78 (s, 3 H), 3.27 (d, J=22.8 Hz, 2 H).

C: (3aR,4R,5R,6aS)-5-(Benzoyloxy)4-[(E)-4-(3-chlorophenoxy)-3-oxo-1-butenyl]-hexahydro-2H-cyclopenta[b]furan-2-one (13)

Phosphonate 11 (20.5 g, 70.0 mmol), 2.6 g (62 mmol) of LiCl, and 200 mL of THF were mixed together at 0° C. and 6.10 g (60.4 mmol) of NEt$_3$ was added. Aldehyde 12 (14.0 g, 51.1 mmol) dissolved in 50 mL of CH$_2$Cl$_2$ was then added dropwise. After 1 h, the reaction was poured into 200 mL of a 1/1 mixture of saturated NH$_4$Cl/ethyl acetate, the layers were separated, and the aqueous layer was extracted with ethyl acetate (2×100 mL). Combined organic layers were dried over MgSO$_4$, filtered, concentrated, and the residue was chromatographed on silica gel eluting with ethyl acetate/hexanes, 3/2, to afford 16.2 g (72%) of 13 as a white crystalline solid, m.p.=101.0–102.0° C. $^1$H NMR δ 8.0–7.9 (m, 2 H), 7.62–7.52 (m, 1 H), 7.50–7.38 (m, 2 H), 7.18 (t, J=8.2 Hz, 1 H), 7.0–6.82 (m, 3 H), 6.75–6.70 (m, 1 H), 6.54 (d, J=15.1 Hz, 1 H), 5.32 (q, J=6.2 Hz, 1 H), 5.12–5.05 (m, 1 H), 4.66 (s, 2 H), 3.0–2.8 (m, 3 H), 2.7–2.2 (m, 3 H).

D: (3aR,4R,5R,6aS)-5-(Benzoyloxy)-4-[(E)-(3R)-4-(3-chlorophenoxy)-3-hydroxy-1-butenyl]-hexahydro-2H-cyclopenta[b]furan-2-one (14)

To a solution of 9.70 g (22.0 mmol) of enone 13 in 60 mL of THF at −23° C. was added dropwise a solution of 11.1 g (34.6 mmol) of (−)-B-chlorodiisopino-campheylborane in 30 mL of THF. After 4 h, the reaction was quenched by the dropwise addition of 5 mL of methanol and then warmed to room temperature. After pouring into 200 mL of a 2/1 mixture of ethyl acetate/saturated NH$_4$Cl, the layers were separated, and the aqueous phase was extracted with ethyl acetate (2×100 mL). Combined organic layers were dried over MgSO$_4$, filtered, concentrated, and the residue was chromatographed on silica gel eluting with ethyl acetate/hexanes, 3/2, to afford 4.7 g (48%) of 14 as a white solid, m.p.101.0–102.5° C. $^1$H NMR δ 8.05–7.95 (m, 2 H), 7.62–7.40 (m, 3 H), 7.18 (t, J=8.0 Hz, 1 H), 7.0–6.92 (m, 1 H), 6.85 (t, J=2.1 Hz, 1 H), 6.77–6.70 (m, 1 H), 5.85 (d of d, J =6.2,15.5 Hz, 1 H), 5.72 (d of d, J=4.5,15.5 Hz, 1 H), 5.30 (q, J=5.8 Hz, 1 H), 5.12–5.04 (m, 1 H), 4.58–4.48 (m, 1 H), 3.92 (d of d, J=3.5, 9.3 Hz, 1 H), 3.80 (d of d, J=7.3, 9.4 Hz, 1 H), 2.9–2.2 (m, 8 H).

E: (3aR,4R,5R,6aS)-4-[(E)-(3R)-4-(3-Chlorophenoxy)-3-(tetrahydropyran-2-yloxy)-1-butenyl]-5-(tetrahydropyran-2-yloxy)-hexahydro-2H-cyclopenta[b]furan-2-one (16)

To a mixture of 5.1 g (11.5 mmol) of 14 in 200 mL of methanol was added 1.7 g (12 mmol) of K$_2$CO$_3$. After 1 h, the mixture was poured into 100 mL of 0.5 M HCl and extracted with ethyl acetate (3×100 mL). The combined organic layers were washed successively with water (2×100 mL) and saturated NaCl (2×100 mL). The organic layer was dried over MgSO$_4$, filtered, and concentrated to afford 4.85 g of crude diol 15, which was used in the next step without further purification.

To a mixture of 4.85 g of crude 15 and 2.4 g (28 mmol) of 3,4-dihydro-2H-pyran in 75 mL of CH$_2$Cl$_2$ at 0° C. was added 370 mg (1.9 mmol) of p-toluenesulfonic acid monohydrate. After stirring for 45 min, the reaction was poured into 40 mL of saturated NaHCO$_3$, layers were separated, and the aqueous layer was extracted with CH$_2$Cl$_2$ (2×40 mL). The combined organic layers were dried over MgSO$_4$, filtered, and concentrated. The residue was chromatographed on silica gel eluting with 40% ethyl acetate in hexanes, to afford 6.0 g (100%) of 16 as an oil. $^1$H NMR (CDCl$_3$) δ (characteristic peaks only) 7.25–7.14 (m, 1 H), 6.95–6.87 (m, 2 H), 6.83–6.72 (m, 1 H), 5.8–5.4 (m, 4 H), 5.1–4.8 (m, 2 H).

F: (13E)-(9S,11R,15R)-11,15-Bis(tetrahydropyran-2-yloxy)-16-(3-chlorophenoxy) -2,3,4,5,6,17,18,19,20-nonanor-9-triethylsilyloxy-13-prostenol Triethylsilyl Ether (18)

To a suspension of 400 mg (10.5 mmol) of lithium aluminum hydride in 20 mL of THF at 0° C. was added dropwise a solution of 4.5 g (8.8 mmol) of lactone 16 in 20 mL of THF. After 1 h at 0° C. the mixture was cautiously poured into 100 mL of a 1/1 mixture of ice-cold saturated NH$_4$Cl/ethyl acetate. The layers were separated, and the aqueous layer was extracted with ethyl acetate (2×50 mL). The combined organic layers were dried over MgSO$_4$, filtered, and concentrated to afford 4.5 g (100%) of diol 17 which was used in the next step without further purification.

Triethylsilyl chloride (3.0 g, 20 mmol) was added to a mixture of 4.5 g (8.8 mmol) of crude 17, 40 mL of DMF, 1.85 g (27.0 mmol) of imidazole, and 310 mg (2.5 mmol) of 4-(dimethylamino)pyridine. After 2 h, the reaction was poured into 100 mL of a 1/1 mixture of ethyl acetate/ saturated NH$_4$Cl, layers were separated, and the aqueous layer was extracted with ethyl acetate (2×25 mL). The combined organic layers were washed with water (3×25 mL), dried over MgSO$_4$, and concentrated. The residue was chromatographed on silica gel eluting with 20% ethyl acetate in hexane to afford 5.2 g (80%) of 18. $^1$H NMR (CDCl$_3$) δ (characteristic peaks only) 7.22–7.12 (m, 1 H), 6.95–6.88 (m, 2 H), 6.83–6.71 (m, 1 H), 5.8–5.4 (m, 4 H), 5.1–4.8 (m, 2 H), 1.0–0.85 (m, 18 H), 0.7–0.5 (m, 12 H).

G: (13E)-(9S,11R,15R)-11,15-Bis(tetrahydropyran-2-yloxy)-16-(3-chlorophenoxy) -2,3,4,5,6,17,18,19,20-nonanor-9-triethylsilyloxy-13-prostenal (19)

To a mixture of 1.6 g (12.6 mmol) of oxalyl chloride and 15 mL of CH$_2$Cl$_2$ at −78° C. was added dropwise a solution of 1.54 g (19.7 mmol) of DMSO in 2 mL of CH$_2$Cl$_2$. After 10 min, 4.6 g (6.2 mmol) of bissilane 18 in 8 mL of CH$_2$Cl$_2$ was added dropwise. After 95 min, 3.0 g (30 mmol) of NEt$_3$ was added. The mixture was then warmed to room temperature and poured into 70 mL of saturated NH$_4$Cl. The solution was extracted with of CH$_2$Cl$_2$ (3×70 mL) and the combined organic layers were dried over MgSO$_4$, filtered, and concentrated. The residue was chromatographed on silica gel eluting with 20% ethyl acetate in hexane to afford 2.06 g (53%) of 19 as well as 1.5 g (26%) recovered 18. $^1$H NMR (CDCl$_3$) δ (characteristic peaks only) 9.78 (t, J=1.4 Hz, 1 H), 7.22–7.12 (m, 1 H), 6.95–6.88 (m, 2 H), 6.83–6.71 (m, 1 H), 5.8–5.4 (m, 4 H) 5.14.8 (m, 2 H), 1.0–0.85 (m, 18 H), 0.7–0.5 (m, 12 H).

H: (5Z,13E)-(9S,11R,15R)-11,15-Bis(tetrahydropyran-2-yloxy)-16-(3-chloro-phenoxy) -2,3,4,17,18,19,20-heptanor-9-triethylsilyloxy-5,13-prostadienoic Acid Methyl Ester (21)

To a solution of 1.35 g (4.24 mmol) of phosphonate 20 and 2.60 g (9.84 mmol) of 18-crown-6 in 20 mL of THF at −78° C. was added dropwise 6.9 mL (3.45 mmol) of a 0.5 M solution of potassium hexamethyldisilazane in toluene. After stirring for 15 min, a solution of 1.65 g (2.64 mmol) of aldehyde 19 in 20 mL of THF was added dropwise. One hour later, the mixture was poured into 100 mL of saturated NH$_4$Cl/ethyl acetate, 1/1, layers were separated, and the aqueous layer was extracted with ethyl acetate (3×30 mL). The combined organic layers were dried over MgSO$_4$, filtered, concentrated and the residue was chromatographed on silica gel eluting with 20% ethyl acetate in hexane to afford 1.135 g (63%) of 21. $^1$H NMR (CDCl$_3$) δ (characteristic peaks only) 7.22–7.11 (m, 1 H), 6.97–6.86 (m, 2 H), 6.85–6.75 (m,1 H), 6.4–6.2 (m, 1 H), 5.8–5.32 (m, 3 H), 3.66 (s, 3 H).

I: (5Z,13E)-(9S,11R,15R)-11,15-Bis(tetrahydropyran-2-yloxy)-16-(3-chlorophenoxy) -2,3,4,17,18,19,20-heptanor-9-triethylsilyloxy-5,13-prostadien-1-ol (22)

To a solution of 850 mg (1.25 mmol) of ester 21 in 10 mL of THF at 0° C. was added 2.4 mL (3.6 mmol) of a 1.5 M solution of diisobutylaluminum hydride in toluene. After 1 h, the mixture was poured into 20 mL of saturated NH$_4$Cl and was extracted with ethyl acetate (3×20 mL). Combined organic layers were dried over MgSO$_4$, filtered, and concentrated down to 800 mg (98%) of 22 as an oil. $^1$H NMR (CDCl$_3$) a (characteristic peaks only) 7.25–7.15 (m, 1 H), 6.97–6.90 (m, 2 H), 6.86–6.75 (m, 1 H), 5.81–5.41 (m, 4 H).

J: (5Z,13E)-(9S,11R,15R)-11,15-Bis(tetrahydropyran-2-yloxy)-16-(3-chlorophenoxy)-3-oxa-17,18,19,20-tetranor-9-triethylsilyloxy-5,13-prostadienoic Acid Isopropyl Ester (23)

To a solution of 415 mg (6.37 mmol) of alcohol 22 in 4 mL of THF at −78° C. was added dropwise 0.35 mL (0.87 mol) of a 2.5 M solution of n-BuLi in hexane. After 15 min, this solution was transferred via syringe to a-78° C. solution of 195 mg (1.08 mmol) of isopropyl bromoacetate in 2 mL of THF. The mixture was kept at −78° C. for 40 min, warmed to room temperature overnight, and then poured into 20 mL of a 1/1 mixture of saturated NH$_4$Cl/ethyl acetate. Layers were separated, and the aqueous layer was extracted with ethyl acetate (2×10 mL). The combined organic layers were dried over MgSO$_4$, filtered, concentrated, and the residue was chromatographed on silica gel (20% ethyl acetate in hexane) to afford 242 mg (53%) of 23 as an oil. $^1$H NMR (CDCl$_3$) δ (characteristic peaks only) 7.24–7.15 (m, 1 H), 6.97–6.90 (m, 2 H), 6.86–6.75 (m, 1 H), 5.81–5.41 (m, 4 H), 1.57 (d, J=5.7 Hz, 6 H).

K: (5Z, 13E)-(9S,11R, 15R)-16-(3-Chlorophenoxy)-3-oxa-17,18,19,20-tetranor -9,11,15-trihydroxy-5,13-prostadienoic Acid Isopropyl Ester (5)

To a solution of 230 mg (0.32 mmol) of silane 23 in 5 mL of THF at room temperature was added 0.33 mL (0.33 mmol) of a 1 M solution of BU$_4$NF in THF. After 20 min, the reaction was poured into 4 mL of saturated NH$_4$Cl and was extracted with ethyl acetate (4×5 mL). The combined organic layers were dried over MgSO$_4$, filtered, concentrated, and the residue was chromatographed on silica gel (ethyl acetate/hexane, 1/1), to afford 126 mg (65%) of desilylated compound 24.

To 120 mg of 24 in 5 mL of methanol was added 0.4 mL of 2 M HCl. After 1 h, the mixture was added to 3 mL of saturated NaHCO$_3$, and the resulting mixture was extracted with ethyl acetate (3×8 mL). Combined organic layers were dried over MgSO$_4$, filtered, concentrated. The resulting residue was then chromatographed on silica gel eluting with ethyl acetate to afford 54 mg (56%) of 5. $^{13}$C NMR (CDCl$_3$) δ 169.92 (C), 159.26 (C), 135,13 (CH), 134.95 (CH), 134.81 (C), 124.93 (CH), 121.22 (CH), 115.06 (CH), 113.08 (CH), 77.75 (CH), 72.02 (CH), 71.94 (CH$_2$), 70.76 (CH$_2$), 68.77 (CH), 67.78 (CH$_2$), 66.50 (CH$_2$), 55.46 (CH), 49.93 (CH), 42.47 (CH$_2$), 25.85 (CH$_2$), 21.75 (CH$_3$). CI MS, m/z calcd. for C$_{24}$H$_{34}$O$_7$Cl$_1$ (MH$^+$), 469.1993, found 469.1993.

EXAMPLE 2

Synthesis of 13,14-Dihydrofluprostenol Isopropyl Ester

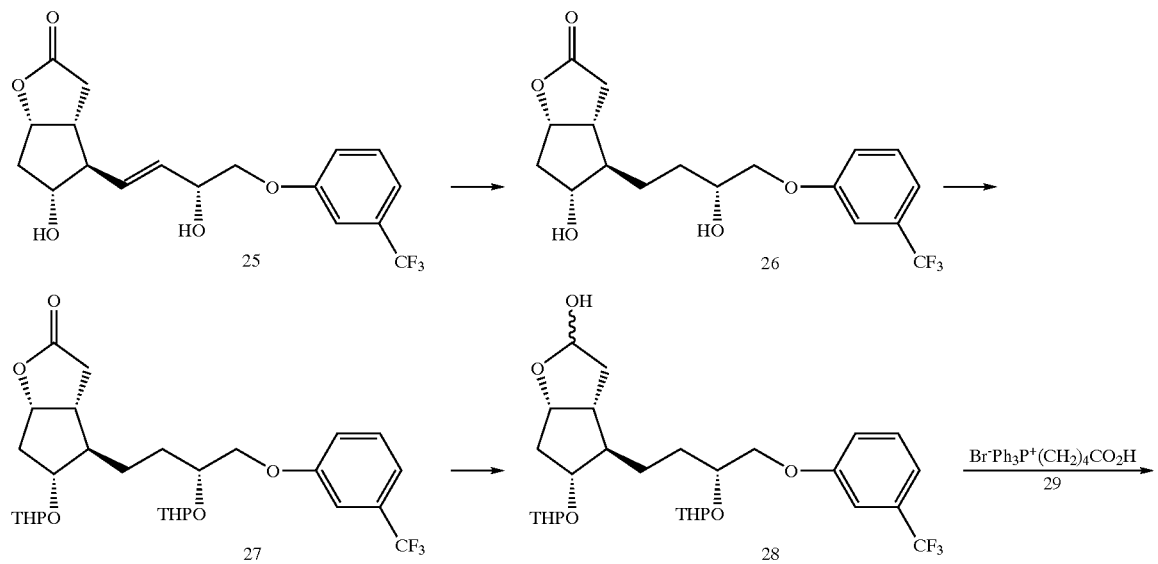

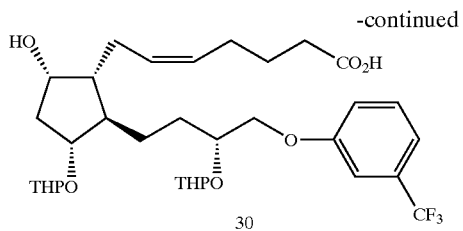
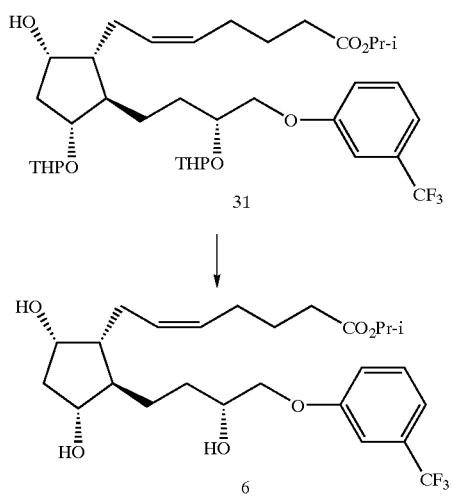

A: (3aR,4R,5R,6aS)-5-Hydroxy-4-[(3R)-4-(3-trifluoromethylphenoxy)-3-hydroxy-1-butyl]-hexahydro-2H-cyclopenta[b]furan-2-one (26)

A mixture of 1.2 g (3.2 mmol) of diol 25 (for synthesis of diol 25, see U.S. Pat. No. 4,321,275) and 0.05 g of 10% (wt/wt) Pd/C in 20 mL of methanol was hydrogenated at 30 psi for 1.5 hours. After filtration through a short pad of Celite® concentration afforded 1.2 g (100%) of 26 as a colorless oil. $^1$H NMR (CDCl$_3$) δ 7.44 (m, 2 H), 7.12 (m, 2 H), 4.95 (dt, 1 H), 4.15–3.80 (m, 4 H), 2.82 (dd, J=10.8, 1 H), 2.55 (m, 2 H), 2.3 (m, 1 H), 2.1–1.3 (m, 6 H).

B: (3aR,4R,5R,6aS)-5-(Tetrahydropyran-2-yloxy)-4-[(3R)-4-(3-trifluoromethylphenoxy)-3-(tetrahydropyran-2-yloxy)-1-butyl]-hexahydro-2H-cyclopenta[b]furan -2-one (27)

A mixture of 1.2 g (3.2 mmol) of diol 26 and 0.05 g of p-toluenesulfonic acid monohydrate in 100 mL of CH$_2$Cl$_2$ at 0° C. was treated with 3,4-dihydro-2H-pyran (1.1 ml, 12 mmol) and the solution was stirred for 2 h at 0° C. After pouring into saturated NaHCO$_3$, phases were separated and the organic layer was dried over MgSO$_4$, filtered, concentrated, and purified by chromatography on silica gel (1/1, hexanes/EtOAc) to afford 1.1 g of 27 as a clear, colorless oil. $^1$H NMR (CDCl$_3$) δ 8.04 (dd, J=7.0,1.6,1 H), 7.44 (m, 2 H), 7.12 (m, 1 H), 4.95 (dt, 1 H), 4.8 (m, 1 H), 4.7 (m, 2 H), 4.15–3.80 (m, 4 H), 3.5 (m, 2 H), 2.82 (dd, J=10.8,1 H), 2.55 (m, 2 H), 2.3 (m, 1 H), 2.1–1.3 (m, 6 H).

C: (5Z)-(9S,11R,15R)-11,15-Bis(tetrahydropyran-2-yloxy)-9-hydroxy-17,18,19,20-tetranor-16-(3-trifluoromethylphenoxy)-5-prostenoic Acid Isopropyl Ester (31)

To a solution of 2.1 g (3.9 mmol) of 27 in 100 mL of THF at −78° C. was added 3.9 mL (5.8 mmol) of a 1.5 M solution of diisobutylaluminum hydride in toluene. The solution was stirred for 2 h, then quenched by the sequential addition of 0.4 mL of isopropanol at −78° C. followed by 0.4 mL of water at 23° C. Volatiles were removed under reduced pressure and the aqueous solution was extracted with Et$_2$O/EtOAc (1/1). Organic extracts were dried over MgSO$_4$, filtered, and concentrated to furnish 1.9 g of lactol 28.

To a 250 mL 3-necked round bottom flask equipped with a mechanical stirrer and a thermometer were added anhydrous DMSO (100 mL) and NaH (80% dispersion in mineral oil; 0.48 g, 16 mmol). The mixture was heated to 75° C. (internal) for 30 min, after which it was allowed to cool to room temperature for 1 h. Phosphonium bromide 29 (3.5 g, 8 mmol) was then added. After stirring for 30 minutes, 1.9 g (3.5 mmol) of lactol 28 in 50 mL of DMSO was added, and the resulting solution was heated to 50° C. for 2 h and then brought to room temperature for 16 h. The solution was poured into 100 mL of water and approximately 2 mL of 50% NaOH added. The aqueous phase was extracted with ether (3×100 mL), then made acidic (pH=5.5) by the addition of a 10% citric acid solution, and extracted with Et$_2$O/hexanes, 2/1 (3×100 mL). The combined organic extracts were dried over MgSO$_4$, filtered, and concentrated to afford 1.9 g of 30 as a colorless oil.

To 1.9 g of carboxylic acid 30 dissolved in 10 mL acetone was added 0.95 g (6.0 mmol) of DBU and 1.0 g (6.1 mmol) of isopropyl iodide at 23° C. After 16 h, the solution was poured into 100 mL of water and extracted with 100 mL of EtOAc. The organic extract was dried over MgSO$_4$, filtered, concentrated, and purified by silica gel chromatography (3/2, hexanes/EtOAc) to afford 1.9 g of isopropyl ester 31 as a colorless oil. $^1$H NMR (CDCl$_3$) δ 7.44 (t, 1 H), 7.12 (d, 1 H), 7.12 (dd, 2 H), 5.5–5.3 (m, 2 H), 4.99 (heptet, 1 H), 4.15–3.80 (m, 4 H), 2.82 (dd, J=10.8,1 H), 2.55 (m, 2 H), 2.3 (m, 1 H), 2.1–1.3 (m, 24 H), 1.23 (s, 3 H), 1.20 (s, 3 H).

D: (5Z)-(9S,11R,15R)-17,18,19,20-Tetranor-16-(3-trifluoromethylphenoxy)-9,11,15-trihydroxy-5-prostenoic Acid Isopropyl Ester (6)

Ester 31 (1.9 g, 2.8 mmol) was dissolved in 14 mL of a mixture of AcOH/THF/H$_2$O (4/2/1) and the solution was heated to 50° C. for 1 h, allowed to cool to 23° C., poured into a saturated solution of NaHCO$_3$, and extracted with Et$_2$O (2×100 mL) and EtOAc (100 mL). The combined organic extracts were dried over MgSO$_4$, filtered, concentrated, and purified by silica gel chromatography (1/1, hexanes/EtOAc) to furnish 0.5 g of triol 6 as a clear, colorless oil. $^1$H NMR (CDCl$_3$) δ 7.44 (t, J=7.8,1 H), 7.12 (dd, J=7.8, 2.0,1 H), 7.12 (ddd, J=15.6, 7.2, 2.0, 2 H), 5.5–5.3 (m, 2 H), 4.99 (heptet, J=6.3,1 H), 4.15–3.80 (m, 4 H), 3.2 (d, 1 H), 2.95 (s, 1 H), 2.82 (dd,J=10.8,1 H), 2.75 (d, J=5.9,1 H), 2.55 (m, 2 H), 2.3 (m, 1 H), 2.1–1.3 (m, 24 H), 1.23 (s, 3 H), 1.20 (s, 3 H). $^{13}$C NMR (CDCl$_3$) δ 173.5, 158.7, 132.1, 131.5, 130.0, 129.5, 129.2, 123.3, 120.8, 117.7, 117.6, 111.4, 111.4, 78.6, 74.4, 72.4, 69.9, 67.6, 52.6, 51.7, 42.5, 34.0, 31.5, 29.4, 26.8, 26.6, 24.9, 21.7.

EXAMPLE 3

Synthesis of Cloprostenol-1-ol (7)

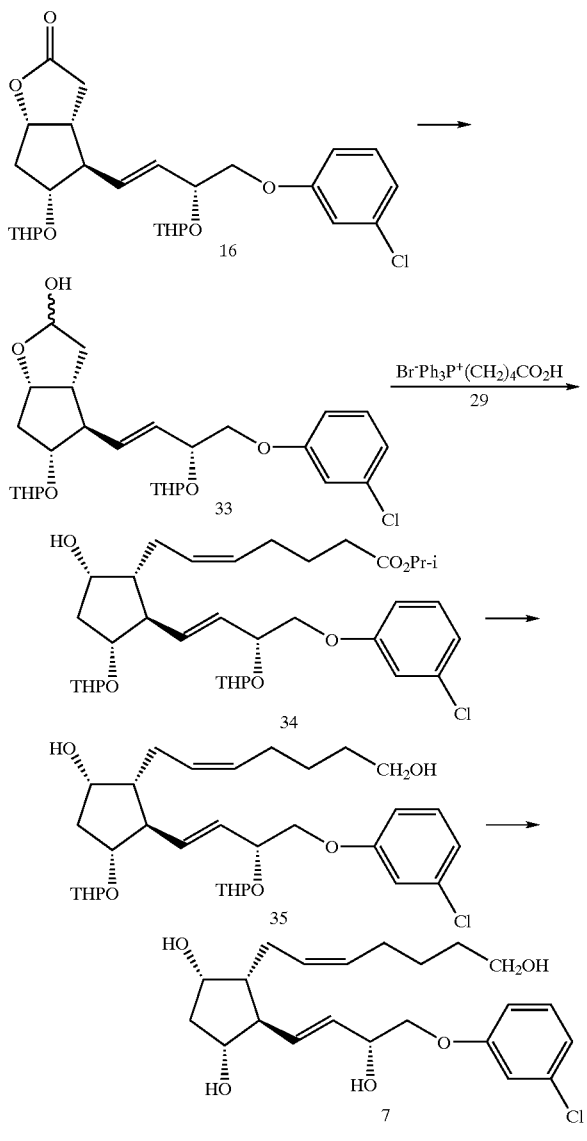

A: (5Z, 13E)-(9S,11R,15R)-11,15-Bis(tetrahydropyran-2-yloxy)-16-(3-chlorophenoxy)-9-hydroxy-17,18,19,20-tetranor-5,13-prostadienoic Acid Isopropyl Ester (34)

A 1.5 M solution of diisobutylaluminum hydride in toluene (10 mL, 15 mmol) was added dropwise to a solution of 5.8 g (11.4 mmol) of lactone 16 in 55 mL of THF at −78° C. After 1 h, 10 mL of methanol was added dropwise, and the mixture was stirred for 10 min at −78° C. before being warmed to room temperature. The mixture was then poured into 100 mL of a 1/1 solution of saturated aqueous potassium sodium tartrate/ethyl acetate and stirred. After separating layers, the aqueous phase was extracted with ethyl acetate (2×40 mL). Combined organic layers were dried over MgSO$_4$, filtered, concentrated, and purified by silica gel chromatography (3/2, ethyl acetate/hexane), to afford 4.4 g (76%) of lactol 33, which was used immediately in the next step.

A 1 M solution of potassium t-butoxide in THF (50.0 ml) was added dropwise to 12.1 g (27.3 mmol) of phosphonium salt 29 in 100 mL of THF at 0° C. After 30 min, a solution of 4.4 g (8.6 mmol) of lactol 33 in 20 mL of THF was added dropwise, and the mixture was stirred at room temperature overnight. The solution was then poured into 150 mL of a 1/1 mixture of ethyl acetate/saturated NH$_4$Cl. Layers were separated and the aqueous layer was extracted with ethyl acetate (2×100 mL). Combined organic layers were dried over MgSO$_4$, filtered, concentrated, and the residue was redissolved in 80 mL of acetone. To this was added 6.5 g (45 mmol) of DBU followed by 7.3 g (43 mmol) of isopropyl iodide. After stirring overnight, the reaction was poured into 100 mL of a 1/1 mixture of ethyl acetate/saturated NH$_4$Cl. Layers were then separated and the aqueous phase was further extracted with ethyl acetate (2×100 mL). The combined organic layers were dried over MgSO$_4$, filtered, concentrated, and purified by silica gel chromatography (40% ethyl acetate in hexane) to afford 2.92 g (53% from lactone 16) of ester 34.

B: (5Z,13E)-(9S,11R,15R)-16-(3-Chlorophenoxy)-17,18,19,20-tetranor-9,11,15-trihydroxy-5,13-prostadienol (7)

A solution of 500 mg (0.79 mmol) of 34 in 10 mL of THF was added dropwise to 61 mg (1.60 mmol) of lithium aluminum hydride in 20 mL of THF at 0° C. After 40 min, the reaction was carefully poured into 15 mL of saturated NH$_4$Cl, and the mixture was then extracted with ethyl acetate (3×40 mL). Combined organic layers were dried over MgSO$_4$, filtered, and concentrated to afford 500 mg of crude 35.

To a solution of 500 mg of 35 in 20 mL of methanol was added 0.5 mL of 2 M HCl. After 1 h, the reaction was quenched with 20 mL of saturated NaHCO$_3$ and the mixture was extracted with ethyl acetate (4×30 mL). The combined organic layers were dried over MgSO$_4$, filtered, and concentrated. Silica gel chromatography (EtOAc) provided 101 mg (31% from 34) of 7. $^{13}$C NMR (CDCl$_3$) δ 159.27 (C), 135.44 (CH), 134.82 (C), 130.64 (CH), 130.26 (CH), 128.23 (CH), 121.25 (CH), 115.07 (CH), 113.08 (CH), 77.35 (CH), 72.35 (CH), 71.90 (CH$_2$), 70.89 (CH), 62.22 (CH$_2$), 55.40 (CH), 49.87 (CH), 42.79 (CH$_2$), 31.83 (CH$_2$), 26.77 (CH$_2$), 25.60 (CH$_2$), 25.33 (CH$_2$). Cl MS m/z calcd for C$_{22}$H$_{32}$O$_5$Cl$_1$ (MH$^+$) 411.1938, found 411.1938.

EXAMPLE 4

Synthesis of 13,14-Dihydrocloprostenol-1-ol Pivaloate (8)

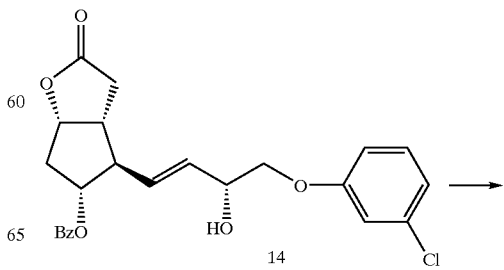

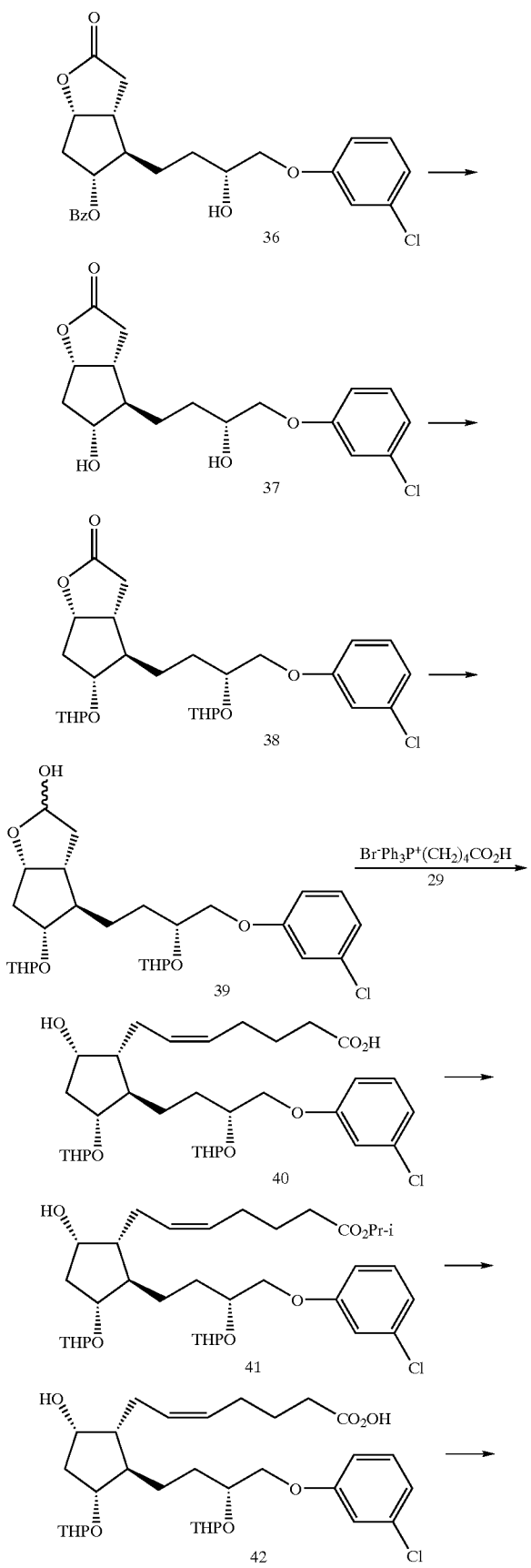

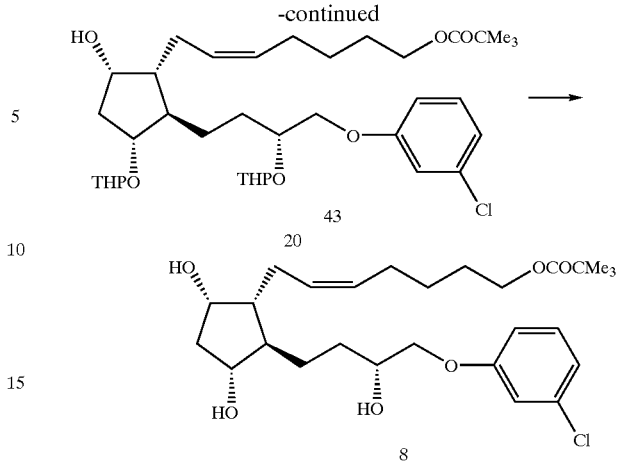

A: (3aR,4R,5R,6aS)-4-[(3R)-4-(3-Chlorophenoxy)-3-hydroxybutyl]-5-hydroxy-hexahydro-2H-cyclopenta[b]furan-2-one (37):

A mixture of 2.4 g (5.4 mmol) of 14 and 250 mg of 10% (wt/wt) Pd/C in 35 mL of ethyl acetate was hydrogenated at 40 psi for 1 h. After filtration through a short pad of Celite®, the filtrate was evaporated down to 2.3 g (100%) of hydrogenated product 36.

The crude benzoate 36 was dissolved in 25 mL of methanol, and 610 mg (4.4 mmol) of $K_2CO_3$ was added. After 3.5 h, the mixture was poured into 100 mL of water/ethyl acetate (1/1). Layers were separated, and the aqueous phase was further extracted with ethyl acetate (2×50 mL). The combined organic layers were dried over $MgSO_4$, filtered and concentrated. Silica gel chromatography (EtoAc) provided 1.50 g (82%) of 37 as a white solid, m.p.=102.0–103.5° C. $^1$H NMR δ 7.22 (t, J=8.2 Hz, 1 H), 7.0–6.94 (m, 1 H), 6.91–6.88 (t, J=2.1 Hz, 1 H), 6.83–6.77 (m, 1 H), 4.97 (dt, J=3.0, 8.3 Hz, 1 H), 4.12–3.91 (m, 3 H), 3.82 (dd, J=7.4, 9.0 Hz, 1 H), 2.85 (dd, J=8.0, 16.5 Hz, 1 H), 2.6–1.4 (m, 11 H).

B: (3aR,4R,5R,6aS)-4-[(3R)-4-(3-Chlorophenoxy)-3-(tetrahydropyran-2-yloxy)butyl]-5-(tetrahydropyran-2-yloxy)-hexahydro-2H-cyclopenta[b]furan-2-one (38)

Diol 37 (3.4 g, 10 mmol) and 2.2 g (26 mmol) of 3,4-dihydro-2H-pyran were dissolved in 80 mL of $CH_2Cl_2$, and 240 mg (1.3 mmol) of p-toluenesulfonic acid monohydrate was added at 0° C. After 1 h, the reaction was poured into 50 mL of saturated $NaHCO_3$ and the mixture was extracted with $CH_2Cl_2$ (3×40 mL). The combined organic layers were dried over $MgSO_4$, filtered, concentrated, and the residue was chromatographed on silica gel (hexane/ethyl acetate, 1/1) to afford 4.5 g (87%) of bis-THP ether 38.

C: (5Z)-(9S,11R,15R)-11,15-Bis(tetrahydropyran-2-yloxy)-16-(3-chlorophenoxy)-9-hydroxy-17,18,19,20-tetranor-5-prostenoic Acid Isopropyl Ester (41)

A 1.5 M solution of diisobutylaluminum hydride in toluene (1.8 mL, 2.7 mmol) was added to the solution 1.05 g (2.06 mmol) of 38 in 10 mL of THF at –78° C. After 1 h, 4 mL of methanol was added and the mixture was warmed to 25° C., then poured into 40 mL of ethyl acetate/saturated aqueous potassium sodium tartrate (1/1). Layers were separated and the aqueous phase was further extracted with ethyl acetate (3×30 mL). The combined organic layers were then dried over $MgSO_4$, filtered, concentrated, and the residue was chromatographed on silica gel (ethyl acetate) to afford 740 mg (70%) of lactol 39.

A 1.5 M solution of potassium t-butoxide in THF (8.6 mL, 8.6 mmol) was added dropwise to a mixture of 15 mL of THF and 1.92 g (4.33 mmol) of phosphonium salt 29 at 0° C. After stirring for 1 h, a solution of 740 mg (1.45 mmol) of lactol 39 in 5 mL of THF was added dropwise, and the reaction was allowed to 10 warm to 25° C. overnight. The mixture was then poured into 100 mL of ethyl acetate/ saturated $NH_4Cl$ (1/1). Layers were separated, and the aqueous phase was further extracted with ethyl acetate (2×70 mL). Combined organic layers were dried over $MgSO_4$, filtered, and concentrated to afford 1.6 g of crude acid 40.

Crude acid 40 (1.6 g) was dissolved in 11 mL of acetone and cooled to 0° C., then 850 mg (5.6 mmol) of DBU was added dropwise to the solution. The resulting mixture was stirred for 15 min at 0° C. and 30 min at 25° C., after which 850 mg (5.0 mmol) of isopropyl iodide was added. The reaction was stirred overnight and poured into 100 mL of ethyl acetate/saturated $NH_4Cl$ (1/1). Layers were separated, and the aqueous phase was further extracted with ethyl acetate (2×50 mL). Combined organic layers were dried over $MgSO_4$, filtered and concentrated. The resulting residue was purified by silica gel chromatography (ethyl acetate/ hexanes, 3/2) to afford 560 mg (61% from lactol 39) of isopropyl ester 41.

D: (5Z)-(9S,11R,15R)-16-(3-Chlorophenoxy)-17,18,19,20-tetranor-9,11,15-trihydroxy-5-prostenol Pivaloate (8)

A solution of 400 mg (0.63 mmol) of 41 in 5 mL of THF was added dropwise to a suspension of 35 mg (0.92 mmol) of lithium aluminum hydride in 5 mL of THF at 0° C. After 2 h, the reaction was poured into 50 mL of a 1/1 mixture of ethyl acetate/saturated $NaHCO_3$. The layers were then separated, and the aqueous phase was extracted with ethyl acetate (2×2 mL). Combined organic layers were dried over $MgSO_4$, filtered, and concentrated. The resulting residue was purified by silica gel chromatography (ethyl acetate) to afford 350 mg (95%) of diol 42.

Pivaloyl chloride (90 mg, 0.75 mmol) was added to a mixture of 350 mg (0.60 mmol) of 42, 60 mg (0.76 mmol) of pyridine, 22 mg (0.18 mmol) of 4-(dimethylamino) pyridine, and 7 mL of $CH_2I_2$. After 1.5 h, the mixture was poured into 30 mL of saturated $NH_4Cl$/ethyl acetate (1/1). Layers were then separated and the aqueous phase was extracted with ethyl acetate (2×20 mL). The combined organic layers were dried over $MgSO_4$, filtered, concentrated, and purified by silica gel chromatography (ethyl acetate/hexane, 3/2) to afford 370 mg (93%) of pivaloate 43.

Water (approximately 10 drops) and concentrated HCl (approximately 3 drops) were added to a solution of 370 mg (0.56 mmol) of 43 in 5 mL of methanol. After stirring overnight, the reaction was quenched by the addition of 20 mL of saturated $NaHCO_3$, and the mixture was extracted with ethyl acetate (3×20 mL). The combined organic layers were dried over $MgSO_4$, filtered, and concentrated. The residue was chromatographed on silica gel (ethyl acetate/ hexane, 3/2), to afford 165 mg (59%) of triol 8. $^{13}C$ NMR ($CDCl_3$) ä 178.77 (C), 159.27 (C), 134.80 (C), 130.20 (CH), 128.62 (CH), 121.19 (CH), 114.97 (CH), 112.97 (CH), 78.50 (CH), 74.46 (CH), 72.31 ($CH_2$), 69.86 (CH), 64.16 ($CH_2$), 52.53 (CH), 51.67 (CH), 42.50 ($CH_2$), 31.51 ($CH_2$), 29.40 ($CH_2$), 28.10 ($CH_2$), 27.12 ($CH_3$), 26.77 ($CH_2$), 26.65 ($CH_2$), 25.77 ($CH_2$). CI MS, m/z calcd for $C_{27}H_{41}O_6Cl_1$ ($MH^+$), 497.2670, found 497.2656

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/ non-racemic or achiral starting materials. (Asymmetric Synthesis by J. D. Morrison and J. W. Scott, Ed., Academic Press Publishers: New York, 1983–1985 (five volumes published over a three year span with chapters contributed by about two dozen authors) and Principles of Asymmetric Synthesis by R. E. Gawley and J. Aube, Ed., Elsevier Publishers: Amsterdam, 1996). They may also be isolated from racemic and non-racemic mixtures by a number of known methods, e.g. by purification of a sample by chiral HPLC (A Practical Guide to Chiral Separations by HPLC, G. Subramanian, Ed., VCH Publishers: New York, 1994; Chiral Separations by HPLC, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios. Also included within the scope of the present invention are the individual isomers substantially free of their respective enantiomers.

EXAMPLE 5

$PGF_{2\alpha}$ analogues are known to contract the iris sphincter of cats and this assay is a generally accepted reference for activity. For this reason, the pupil diameter of cats may be used to define the activity of $PGF_2$,>analogues and, as demonstrated by Stjernschantz and Resul (*Drugs Future*, 17:691–704 (1992)), predict the IOP-lowering potency.

Compounds of the present invention were therefore screened for pupillary constriction in the cat. Data for compounds 6, 7, and 8 are presented in Table 3, below. The response is quantitated as Area 1–5 values (area under the pupil diameter versus time curve from 1–5 hours), and the equivalent response dose ($ED_5$) is estimated from its dose response relationship.

TABLE 3

| Cat Pupil Diameter Response | |
|---|---|
| Compound | $ED_5$ (µg) |
| $PGF_{2\alpha}$ Isopropyl Ester | 0.02 |
| Cloprostenol Isopropyl Ester | 0.01 |
| 6 | 0.2 |
| 7 | 0.02 |
| 8 | 0.06 |

Discussion:

The two standard compounds, $PGF_{2\alpha}$ isopropyl ester and cloprostenol isopropyl ester, produced marked change in cat pupillary diameter, displaying $ED_5$ values of 0.02 and 0.01 µg, respectively. Compound 7 (cloprostenol-1-ol) and compound 8 (13,14-dihydrocloprostenol-1-ol pivaloate), displayed nearly equivalent potency. 13,14-Dihydrofluprostenol isopropyl ester (compound 6) was approximately one order of magnitude less potent, with an $ED_5$ of 0.2 µg.

EXAMPLE 6

In the study presented below, compound 6 (Table 2, above) was tested for IOP-lowering effect in cynomolgus monkey eyes.

The right eyes of the cynomolgus monkeys used in this study were previously given laser trabeculoplasty to induce ocular hypertension in the lasered eye. Animals had been trained to sit in restraint chairs and conditioned to accept experimental procedures without chemical restraint. IOP was determined with a pneumatonometer after light corneal anesthesia with dilute proparacaine. The test protocol included a five-dose treatment regimen because of the typical delayed response to prostaglandins. The designated test formulations were administered to the lasered right eyes, and the normal left eyes remained untreated, although IOP measurements were taken. Baseline IOP values were determined prior to treatment with the test formulation, and then IOP was determined from 1 to 7 hours after the first dose, 16 hours after the fourth dose, and 1 to 4 hours after the fifth dose.

The equivalent response dose ($ED_{20}$) is estimated from the dose response relationship to be the dose producing a 20% peak reduction in IOP.

TABLE 4

Monkey IOP Response

| Compound | $ED_{20}$ (μg) |
|---|---|
| $PGF_{2\alpha}$ Isopropyl Ester | 0.4 |
| 6 | 0.3 |

Discussion:

As can be seen in Table 4, compound 6, the 13,14-dihydro analogue of fluprostenol was quite potent in the monkey IOP model, producing a 20% reduction at 0.3 μg. This was even more potent than the standard compound, $PGF_{2\alpha}$ isopropyl ester.

EXAMPLE 7

Improvement of Optic Nerve Head Blood Flow after One-Week Topical Treatment with Compound 1B in the Rabbit.

Purpose:

A two-way crossover study design was used to compare the effects of Compound 1B (0.004%), topically applied, and dosing vehicle on microvascular optic nerve head blood flow, blood pressure, heart rate, and acid-base balance in fifteen acepromazine-tranquilized Dutch-Belted rabbits.

Methods:

Baseline measurements were taken before treatment and after drug-free washout periods of 14 days. Microvascular optic nerve head (ONH) blood flow was measured with a fundus camera-based Laser Doppler flowmeter (LDf). Thirty microliters o a 0.004% solution of Compound 1B or vehicle was administered in left eyes only q.d. for 7 days. Experimental measurements were made 2 hours after the topical dose was administered on day 8. A sterile 23 gauge intracatheter was inserted into the central ear artery to monitor blood pressure and to take blood samples for blood pH/gas analysis.

Results:

ONH blood flow was significantly increased (p<0.05) in rabbits treated with Compound 1B, when compared to the vehicle treated group. The mean ±SEM percent increase from baseline was 13.4±3.9 in Compound 1B treated animals and −1.0±4.3 in vehicle treated animals. Only small non-significant changes in systemic blood pressure, heart rate, blood gas tensions and pH were present in the Compound 1B treatment group when compared with the vehicle group. The observed mean percent decreases in systemic arterial pH, and $PO_2$ and arterial $pCO_2$ tensions were 0.07±0.09, 1.44±2.03, and 2.59±2.5, respectively.

Conclusion:

One week of once a day topical ocular treatment with Compound 1B significantly increased ONH blood flow in tranquilized Dutch-Belted rabbits, while eliciting minimal systemic acid-base balance disturbances. This suggests that the mechanism responsible for the positive effect on the ONH vasculature involves a local ocular action since the blood flow increase in this study occurred without significant changes in systemic blood pressure or arterial blood gases/pH.

EXAMPLE 8

The following Formulations 1–4 are representative pharmaceutical compositions of the invention for topical use in lowering of intraocular pressure. Each of Formulations 1 through 4 may be formulated in accordance with procedures known to those skilled in the art.

| Ingredient | Amount (wt %) |
|---|---|
| FORMULATION 1 | |
| Compound 5 (Table 2) | 0.002 |
| Dextran 70 | 0.1 |
| Hydroxypropyl methylcellulose | 0.3 |
| Sodium chloride | 0.77 |
| Potassium chloride | 0.12 |
| Disodium EDTA | 0.05 |
| Benzalkonium chloride | 0.01 |
| HCl and/or NaOH | pH 7.2–7.5 |
| Purified water | q.s. to 100% |
| FORMULATION 2 | |
| Compound 6 (Table 2) | 0.01 |
| Monobasic sodium phosphate | 0.05 |
| Dibasic sodium phosphate (anhydrous) | 0.15 |
| Sodium chloride | 0.75 |
| Disodium EDTA | 0.01 |
| Benzalkonium chloride | 0.02 |
| Polysorbate 80 | 0.15 |
| HCl and/or NaOH | pH 7.3–7.4 |
| Purified water | q.s. to 100% |
| FORMULATION 3 | |
| Compound 7 (Table 2) | 0.001 |
| Dextran 70 | 0.1 |
| Hydroxypropyl methylcellulose | 0.5 |
| Monobasic sodium phosphate | 0.05 |
| Dibasic sodium phosphate (anhydrous) | 0.15 |
| Sodium chloride | 0.75 |
| Disodium EDTA | 0.05 |
| Benzalkonium chloride | 0.01 |
| NaOH and/or HCl | pH 7.3–7.4 |
| Purified water | q.s. to 100% |
| FORMULATION 4 | |
| Compound 8 (Table 2) | 0.003 |
| Monobasic sodium phosphate | 0.05 |
| Dibasic sodium phosphate (anhydrous) | 0.15 |
| Sodium chloride | 0.75 |
| Disodium EDTA | 0.05 |
| Benzalkonium chloride | 0.01 |
| HCl and/or NaOH | pH 7.3–7.4 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a composition comprising a therapeutically effective amount of a compound having the absolute stereochemical structure of the following formula (IV):

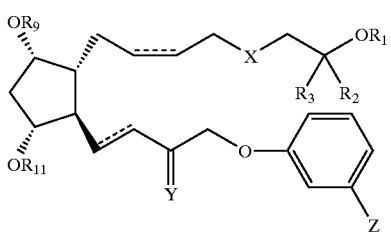

(IV)

wherein:
- $R_1$=H; $C_1$–$C_{12}$ straight-chain or branched alkyl; $C_1$–$C_{12}$ straight-chain or branched acyl; $C_3$–$C_8$ cycloalkyl; or a cationic salt moiety;
- $R_2$, $R_3$=H, or $C_1$–$C_5$ straight-chain or branched alkyl; or $R_2$ and $R_3$ taken together may represent O;
- X=O, S, or $CH_2$;
- ⁓ represents any combination of a single bond, or a cis or trans double bond for the alpha (upper) chain; and a single bond or trans double bond for the omega (lower) chain;
- $R_9$=H, $C_1$–$C_{10}$ straight-chain or branched alkyl, or $C_1$–$C_{10}$ straight-chain or branched acyl;
- $R_{11}$=H, $C_1$–$C_{10}$ straight-chain or branched alkyl, or $C_1$–$C_{10}$ straight-chain or branched acyl;
- Y=O; and Z=Cl or $CF_3$;

with the proviso that when $R_2$ and $R_3$ taken together represent O, then $R_1 \neq C_1$–$C_{12}$ straight-chain or branched acyl; and when $R_2$=$R_3$=H, then $R_1 \neq$ a cationic salt moiety.

2. The method of claim 1, wherein for the compound (IV):
- $R_2$, $R_3$ taken together represent O;
- X=$CH_2$;
- ⁓ represents a cis double bond for the alpha (upper) chain and a trans double or a single bond for the omega (lower) chain; and
- $R_9$ and $R_{11}$=H.

3. The method of claim 2, wherein for the compound (IV): Z=$CF_3$.

4. The method of claim 1, wherein: $R_2$=$R_3$=H, or $R_2$ and $R_3$ taken together represent O; X=O or $CH_2$; and $R_9$=$R_{11}$=H.

5. The method of claim 4, wherein: $R_1$=H, $C_1$–$C_{12}$ straight chain or branched alkyl or cationic salt moiety; and $R_2$ and $R_3$ taken together represent O.

6. The method of claim 5, wherein the compound of formula (IV) is selected from the group consisting of the 15-keto analogues of: cloprostenol, fluprostenol, 3-oxacloprostenol, 13,14-dihydrofluprostenol, and their pharmaceutically acceptable esters and salts.

7. The method of claim 6, wherein the compound of formula (IV) is the 15-keto analogue of fluprostenol isopropyl ester.

8. The method of claim 1, wherein between about 0.01 and about 1000 μg/eye of the compounds of formula (IV) is administered.

9. The method of claim 8, wherein between about 0.1 and about 100 μg/eye of the compound of formula (IV) is administered.

10. The method of claim 9, wherein between about 0.1 and about 10 μg/eye of the compound of formula (IV) is administered.

11. topical ophthalmic composition for the treatment of glaucoma and ocular hypertension comprising an ophthalmically acceptable carrier and a therapeutically effective amount of a compound having the absolute stereochemical structure of the following formula (IV) and being substantially free of the enantiomer of said compound:

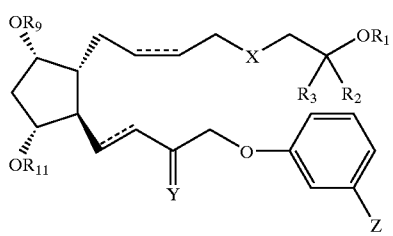

(IV)

wherein:
- $R_1$=H; $C_1$–$C_{12}$ straight-chain or branched alkyl; $C_1$–$C_{12}$ straight-chain or branched acyl; $C_3$–$C_8$ cycloalkyl; or a cationic salt moiety;
- $R_2$, $R_3$ =H, or $C_1$–$C_5$ straight-chain or branched alkyl; or $R_2$ and $R_3$ taken together may represent O;
- X=O, S, or $CH_2$;
- ⁓ represents any combination of a single bond, or a cis or trans double bond for the alpha (upper) chain; and a single bond or trans double bond for the omega (lower) chain;
- $R_9$=H, $C_1$–$C_{10}$ straight-chain or branched alkyl, or $C_1$–$C_{10}$ straight-chain or branched acyl;
- $R_{11}$=H, $C_1$–$C_{10}$ straight-chain or branched alkyl, or $C_1$–$C_{10}$ straight-chain or branched acyl;
- Y=O; and
- Z=Cl or $CF_3$;

with the proviso that when $R_2$ and $R_3$ taken together represent O, then $R_1 \neq C_1$–$C_{12}$ straight-chain or branched acyl; and when $R_2$=$R_3$=H, then $R_1 \neq$ a cationic salt moiety.

12. The composition of claim 11, wherein for the compound (IV):
- $R_2$, $R_3$ taken together represent O;
- X $CH_2$;
- ⁓ represents a cis double bond for the alpha (upper) chain and a trans double or a single bond for the omega (lower) chain; and
- $R_9$ and $R_{11}$=H.

13. The composition of claim 12, wherein for the compound (IV): Z=$CF_3$.

14. The composition of claim 13, wherein the compound of formula (IV) is the 15-keto analogue of 13,14-dihydrofluprostenol isopropyl ester.

15. The method of claim 6, wherein the compound of formula (IV) is the 15-keto analogue of 13,14-dihydrofluprostenol isopropyl ester.

* * * * *